United States Patent [19]

Dean et al.

[11] Patent Number: 5,185,433
[45] Date of Patent: Feb. 9, 1993

[54] CROSS-LINKING PROTEIN COMPOSITIONS HAVING TWO OR MORE IDENTICAL BINDING SITES

[75] Inventors: Richard T. Dean, Dowingtown; John Lister-James, Glenmoore, both of Pa.; Raymond H. Boutin, Wilmington, Del.

[73] Assignee: Centocor, Inc., Malvern, Pa.

[21] Appl. No.: 506,122

[22] Filed: Apr. 9, 1990

[51] Int. Cl.$^5$ .................. C07K 17/06; C07K 15/28; A61K 39/44

[52] U.S. Cl. .................. 530/391.1; 530/387.3; 530/391.3; 530/391.5; 530/391.7; 530/391.9; 530/403; 530/408; 530/409; 424/85.8; 424/85.91; 435/972; 436/512; 436/547; 436/819

[58] Field of Search .............. 530/387, 388, 390, 391, 530/387.3, 391.1, 391.3, 391.5, 391.7, 391.9, 403, 408, 409; 436/512, 547, 819; 435/972; 424/85.8, 85.91

[56] References Cited

U.S. PATENT DOCUMENTS

| | | | |
|---|---|---|---|
| 4,433,059 | 2/1984 | Chang et al. | 436/512 |
| 4,507,234 | 3/1985 | Kato et al. | 530/390 |
| 4,659,839 | 4/1987 | Nicolotti et al. | 548/546 |
| 4,671,958 | 6/1987 | Rodwell et al. | 424/85.91 |
| 4,676,980 | 6/1987 | Segal et al. | 424/85.91 |
| 4,698,420 | 10/1987 | Urnovitz | 530/387 |
| 4,751,286 | 6/1988 | Packard et al. | 530/388 |

FOREIGN PATENT DOCUMENTS

| | | |
|---|---|---|
| 173629 | 3/1986 | European Pat. Off. |
| 188256 | 7/1986 | European Pat. Off. |
| 8901974 | 3/1989 | World Int. Prop. O. |

OTHER PUBLICATIONS

Glennie et al (1987) J. Immunol. 139: 2367–2375.
Brennan et al (1985) Science 229:81–83.
Liu et al (1985) Proc. Natl. Acad. Sci. USA 82:8648–8652.

Primary Examiner—Christine M. Nucker
Assistant Examiner—Kay K. Kim
Attorney, Agent, or Firm—Woodcock Washburn Kurtz Mackiewicz & Morris

[57] ABSTRACT

The present invention provides cross-linked protein compositions consisting of two or more units of a target-specific protein joined by binding sulfhydryl groups on the target-specific protein units to a sulfhydryl-selective cross-linking agent and a method of making the compositions. These cross-linked protein compositions combine an increase in binding affinity due to the presence of multiple identical binding sites and stability to reduction conditions.

10 Claims, No Drawings

CROSS-LINKING PROTEIN COMPOSITIONS HAVING TWO OR MORE IDENTICAL BINDING SITES

FIELD OF THE INVENTION

This invention relates to the field of target-specific protein compositions and, more particularly, to the fields of immunodiagnostics and immunotherapy.

BACKGROUND OF THE INVENTION

Target-specific proteins have been shown to specifically localize and bind to pre-selected target sites, when introduced into an organism. These proteins can be used as carriers of diagnostic and therapeutic agents for specifically localizing such agents to the target. The use of target-specific proteins as carriers involves the binding of the diagnostic or therapeutic agent to the protein to form a conjugate which has the diagnostic or therapeutic properties of the diagnostic or therapeutic agent, and the localization properties of the protein.

The use of monoclonal antibodies and antibody fragments as target-specific carriers of diagnostic or therapeutic agents provides an efficient means of localizing such agents to target tissue. Monoclonal antibodies are highly specific and can be used, for example, for imaging specific target sites or as vehicles to deliver substances to target sites. In recent years numerous monoclonal antibodies have been developed with affinity for targets such as atherosclerotic tissue, fibrin, myosin and tumors, for example. The attachment of radiometals to proteins, especially antibodies and antibody fragments, results in the formation of new radiodiagnostic and radiotherapeutic agents.

Proteins and antibodies have been shown to form stable bonds to radiometals by the use of bifunctional coupling agents. A suitable bifunctional agent is capable of binding radiometals by chelation and can also form a stable linkage to the protein. Thus, the protein or antibody is bound to the radiometal through the bifunctional coupling agent. For example, diethylenetriaminepentaacetic acid (DTPA) has been conjugated onto an antimyosin antibody, and the protein-bound DTPA used to chelate indium-111. See Khaw, et al., Science, 209, 295-97 (1980); Krejcarek, et al., Biochem. Biophys. Res. Comm., 77, 581-85 (1977) and Childs, R. L. and Hnatowich, D. J., J. Nucl. Med., 26, 293 (1985). This approach has also been used where particular diaminodithiol and diamidedithiol chelating agents have been coupled to antibodies and antibody fragments. See Fritzberg, et al., J. Nucl. Med., 27, 957-58 (1986), Eary, J. et al., J. Nucl. Med., 28, 650-51 (1987) and A. R. Fritzberg, et al., Proc. Nat. Acad. Sci. USA, 85, 4025-29 (1988)).

Chelated radiometals and bifunctional coupling agents have been linked to proteins by lysyl side chain amino groups. See EPO Publication No. 188, 256. Chelators have also been site selectively attached to oxidized antibody carbohydrate moieties. See EPO Publication No. 173, 629 and U.S. Pat. No. 4,671,958. Chelators can also be attached by reaction with free sulfhydryl groups. See, for example, U.S. Pat. No. 4,659,839, U.S. Pat. No. 4,671,958 and EPO Publication No. 173,629.

Antibodies and antibody F(ab')2 fragments are symmetrical proteins containing two identical binding sites. The binding of antibodies and antibody F(ab')2 fragments to a target is enhanced relative to the Fab', Fab and Fv fragments which contain only a single binding site. It is believed that the F(ab')2 fragment may be superior to the whole antibody for the preparation of radioimmunotherapeutic and especially radioimmunodiagnostic agents due to a shorter half-life in vivo. See, for example, J. Shani, et al., Nucl. Med. Biol., 16, 33–40 (1989). Further, the absence of the Fc portion of the antibody which can interact non-specifically with Fc receptors may provide additional benefits. See, for example, R. L. Wahl, et al., J. Nucl. Med., 24, 316-25 (1983). The radiolabeled F(ab')2 fragment has been shown to be superior to either IgG or Fab for delivery of activity to tumor sites in models of radioimmunotherapeutic applications. See, for example, R. Sutherland, et al., Canc. Res., 47, 1627–33 (1987), K. Z. Walker, et al., Nucl. Med. Comm., 9, 517–26 (1988).

The F(ab')2 fragment is composed of two identical heavy chain fragments linked by one or more disulfide bridges and two identical light chains each linked to one heavy chain by a disulfide bridge. Exposure of the F(ab')2 fragment to suitable reducing conditions cleaves the interchain disulfide bonds to free sulfhydryls. This reduction gives two identical Fab' fragments, each consisting of a heavy chain fragment and a light chain held together by noncovalent interactions. Each Fab' fragment also contains a single binding site. Examples of reducing conditions that can effect this cleavage include thiols (sulfhydryls) and other reducing agents such as tin (II).

The use of F(ab')2 fragments to prepare radioimmunotherapeutic and radioimmunodiagnostic agents is believed to be superior to whole IgG or monovalent fragments in some instances. The disulfide bond joining the two halves of the F(ab')2 fragment is, however, susceptible to cleavage. There are instances of F(ab')2 cleavage to Fab' in vivo, thus eliminating the advantages of the F(ab')2. See, for example, S. E. Halpern, et al., J. Nucl. Med., 28, 692 (1987). The use of certain radiometals for the formation of radioimmunotherapeutic or radioimmunodiagnostic agents require the use of reducing conditions to adjust the oxidation state of the radiometal. These conditions, when applied to a F(ab')2, can lead to preferential formation of radiolabeled Fab', again precluding the advantages of the F(ab')2. See, for example, A. M. Zimmer, et al., Cancer Res., 47, 1691-94 (1987). In addition, a radiometal chelator linked to a protein by a disulfide will undergo cleavage in vivo. See C. F. Meares, et al., Int. J. Cancer, Supp 2, 99 (1988). The potential advantage of the two binding sites of the F(ab')2 fragment is lost in the situations where reductive cleavage of the interchain disulfide bond occurs.

Reagents have also been described for the covalent linkage of two proteins. Homobifunctional linking reagents, that is linking reagents containing two identical reactive sites, have also been described for cross-linking proteins. The most common examples contain two amine-selective reactive sites or two sulfhydryl selective reactive sites. For example, N,N'-1,4-phenylenedimaleimide has been used to cross-link enzymes and antibodies in the preparation of reagents for enzyme-linked immunoassays. Bis-N-maleimidomethyl ether and N,N'-1,2-phenylenebismaleimide have both been used to prepare bispecific thioether-linked F(ab')2 fragments. See M. J. Glennie, et al., J. Immunol., 139, 2367–75 (1987) and J. M. Frincke, et al., J. Nucl. Med., 692 (1987). These bispecific thioether-linked F(ab')2 fragments consist of two non-identical Fab1 fragments with different binding specificities cross-linked via their sulfhydryls by the bis-maleimide homobifunctional reagent.

In spite of these disclosures, there remains a need for a cross-linked protein composition having at least two identical binding sites, which is suitable for use in immunodiagnostic and immunotherapeutic applications. There is also a need for a simple method of making this protein composition.

SUMMARY OF THE INVENTION

The present invention provides cross-linked protein compositions which comprise at least two target-specific proteins joined by a sulfhydryl-selective cross-linking agent. These compositions are advantageous as they combine an increase in binding affinity due to the presence of multiple binding sites and stability to reduction conditions.

A preferred embodiment of the present invention are cross-linked antibody F(ab')$_2$ fragments. These cross-linked F(ab')$_2$ fragments are especially advantageous as the cross-linking reaction occurs to join two sulfhydryls that were originally attached together as a disulfide. Since these sulfhydryls are located distally to the antigen binding site, the antigen binding site of the cross-linked antibody, or F(ab')$_2$ fragment will be unaffected by the cross-linking reaction.

The present invention also provides methods of preparing diagnostic and therapeutic agents consisting of radioisotopic moieties, bifunctional coupling agents, therapeutic agents or toxic agents attached to cross-linked target-specific protein compositions of the present invention. These diagnostic and therapeutic agents combine the therapeutic or diagnostic properties of the attached agents with the binding affinity and stability against the reducing conditions of the cross-linked target-specific protein compositions.

A preferred embodiment of the present invention uses bifunctional coupling agents which comprise a protein binding function or a reactive site, a chelating agent and an organic linking radical having at least one cleavable site which serves to join the sulfhydryl-selective electrophile of the cross-linked protein composition and the chelating agent.

The radiotherapeutic and radiodiagnostic agents of the present invention may be prepared as kits. The kits have a cross-linked target-specific protein composition bound to a bifunctional coupling agent and formulated in a suitable matrix. The bifunctional coupling agent is bound to a radiometal of therapeutic or diagnostic utility.

DETAILED DESCRIPTION OF THE PREFERRED EMBODIMENTS

Compositions of the present invention comprise at least two target-specific proteins joined by at least one sulfhydryl-selective cross-linking agent. The target-specific protein compositions have identical binding sites and the sulfhydryl-selective cross-linking agent is bound to sulfhydryl groups on the target-specific proteins. As used herein, the term "protein" means peptides or polymers of amino acids, linked as amides, and consisting of five or more amino acids so linked, and the expression "target-specific protein" means a protein which is capable of binding to a pre-selected target.

Suitable target-specific proteins have one or more sulfhydryls or readily reducible disulfide bonds. Such sulfhydryls can result from cysteine residues in the amino acid sequence of the target-specific protein or, alternatively, sulfhydryl groups can be appended to the target-specific protein by binding agents known to introduce sulfhydryls. The cross-linking agents contain two or more reactive sites which form covalent bonds selectively with the sulfhydryls. The cross-linked target-get-specific protein compositions so prepared have two or more identical binding sites for the target. These cross-linked target-specific protein compositions may be used to prepare new therapeutic and diagnostic agents when combined with suitable moieties.

Preferably, target-specific proteins useful in the invention are proteins which, when injected in vivo, will localize to a pre-selected site. Preferred in the invention are antibody fragments. Most preferred are antibody Fab' fragments which, when maintained under reduced conditions, contain one or more sulfhydryls. Other antibody fragments, for example Fab and Fv, can also be used in the invention.

Target-specific proteins not containing free sulfhydryls but containing readily reducible disulfide bonds can be used in the invention by reduction of said disulfide bonds to give sulfhydryls. This reduction can be accomplished using thiol-containing reagents, such as cysteine or dithiothreitol, for example.

Target-specific proteins not containing either a sulfhydryl or a readily reducible disulfide bond can have sulfhydryl groups appended to the target-specific protein by binding reagents known to introduce sulfhydryls. For example, lysyl amino groups can be reacted with 2-iminothiolane in accordance with the method disclosed by J. M. Lambert, et al., Biochem., 17, 5406–16 (1978). Other binding reagents which introduce sulfhydryls onto proteins are well known to those skilled in the art.

Cross-linking agents useful in the invention can be described by the formula E-L-E'; wherein E and E' are sulfhydryl-selective electrophiles and L is an organic linking radical containing two or more sites of attachment for E and E'. E and E' may be identical or different and are selected independently from the group consisting of maleimides, alkyl halides, sulfonate esters and aziridines. Specifically preferred in the invention are N-substituted maleimides. The organic linking radical L is selected from the group consisting of linear or branched alkyl and linear or branched optionally substituted alkyl, aryl and optionally substituted aryl, heteroaromatic and optionally substituted heteroaromatic, and linear or branched alkyl and linear or branched optionally substituted alkyl containing heteroatom substituents for carbon.

The term "optionally substituted" as used herein refers to optional substitution with alkyl, heteroatom and functional groups, such as but not limited to alkoxy, alkyl, hydroxy, amino and carboxy groups. Generally speaking, these optionally substituted groups are unreactive with thiols (sulfhydryls), disulfides, amines and alkylating agents.

L is most preferably represented by the following formula:

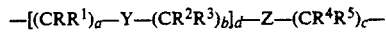

wherein each of R, $R^1$, $R^2$, $R^3$, $R^4$ and $R^5$ are independently selected from hydrogen, optionally substituted alkyl, optionally substituted aryl or heteroaromatic, and most preferably, each of the above-described R groups are hydrogen; a and b are each independently selected from integers from 0 to 6 inclusive, and preferably a and b are 1 or 2; c and d are each independently selected from integers from 0 to 6 inclusive, with the proviso that when d is 0 then Z is a bond and c and d cannot both be 0, and preferably c is 0 and d is 1; Y is selected from the group consisting of a bond, —NH—, —O— or —S—, and preferably Y is —O—; and Z is selected from the group consisting of a bond, Y, —CH$_2$CONH—, and —NHCOCH$_2$—, and preferably Z is a bond.

Specifically preferred cross-linking agents of the invention are exemplified by Compound I and Compound II.

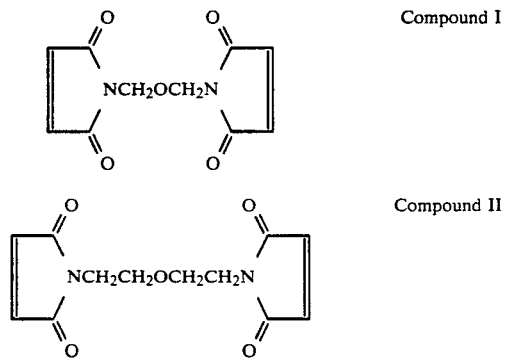

Cross-linked compositions of the invention can be prepared by combining the target-specific protein containing one or more sulfhydryls with the sulfhydryl-selective cross-linking agent. More specifically, a target-specific protein is reacted with a cross-linking agent to produce cross-linked protein composition. Alternatively, additional target-specific protein may be added to yield a cross-linked protein composition. Preferably the reaction occurs in a solution that is buffered between pH 7 and 8. Suitable buffers include phosphates, tris, HEPES and the like. The cross-linked target-specific protein composition is preferably at least twice the molecular weight of the parent target-specific protein unit. Preferably, antibody fragments, and most preferably, Fab' antibody fragments are used as the target-specific proteins. Optimally, the composition should be purified. Purification of the cross-linked target-specific protein composition may be accomplished by gel filtration chromatography, for example.

Preferably, a two-step coupling sequence is used to prepare cross-linked target-specific protein compositions of the present invention. This method uses an excess of the cross-linking agent, which is added to the sulfhydryl containing target-specific protein. After a suitable amount of time, for example about ten minutes to an hour, the excess unbound cross-linking agent is removed and fresh sulfhydryl containing target-specific protein is added to the target-specific protein containing bound cross-linking agent and preferably allowed to react overnight. The process occurs in a suitably buffered solution, preferably between pH 7 and 8.

For compositions where the cross-linking agent is much smaller in molecular weight relative to the target-specific protein, the excess cross-linking reagent is removed, for example, by desalting methods known to those skilled in the art.

After formation of the cross-linked target-specific protein composition, any sulfhydryl reactive sites or readily reducible disulfides still present are preferably blocked or reduced by reaction with a thiol-containing reagent, for example cysteine or dithiothreitol. Preferably, any unreacted sulfhydryls still present after formation of the cross-linked target-specific protein composition are blocked by reaction with a suitable sulfhydryl reactive agent, for example, iodoacetamide or N-ethylmaleimide.

Most preferably, cross-linked target-specific protein compositions of the invention are prepared as follows:

(a) reaction of the sulfhydryl containing target-specific protein with an excess of a cross-linking agent;

(b) removal of excess, unbound cross-linking agent;

(c) addition of fresh sulfhydryl containing target-specific protein to the target-specific protein containing the bound cross-linking agent;

(d) addition of a thiol-containing agent;

(e) addition of a sulfhydryl reactive agent; and (f) purification of the cross-linked target-specific protein composition.

The cross-linked target-specific protein compositions of the invention can be used to prepare new therapeutic agents by the attachment of therapeutic moieties or by attachment of toxic moieties known to have a therapeutic value. As an example, the attachment of protein toxins to antibodies and antibody fragments has been used to generate therapeutic agents where the antibody or antibody fragment is used to site-specifically deliver the toxin. See I. Pastan, M. C. Willingham and D. J. P. Fitzgerald, *Cell*, 47, 641–48 (1986), for example.

Therapeutic moieties may be attached to the cross-linked target-specific protein compositions of the present invention. Suitable therapeutic moieties include, but are not limited to for example, biologically active proteins, chemotherapeutic agents or drugs, such as cis-platin and the like, or toxins in therapeutically effective amounts, including for example, ricin A or N-acetyl melphalan and the like, cell regulators such as the cytokines and the like.

Therapeutic moieties may be attached to the cross-linked target-specific protein composition by methods knwon to those skilled in the art. For example, therapeutic moieties which are small molecules may be bound to the cross-linked target-specific protein composition by active esters or any of the methods of attachment described infra in the discussion of reactive site A. Relatively large molecules may be attached to the cross-linked target-specific protein composition by a cross-linking agent such as glutaraldehyde or bis-imidate esters.

The cross-linked target-specific proteins of the invention can be used to prepare new radiotherapeutic and radiodiagnostic agents by attachment of an appropriate radioisotopic moiety. Various methods of attaching radioisotopic moieties to proteins have been described, and one skilled in the art can apply these methods to the cross-linked target-specific protein compositions of the invention. For example, the attachment of radioisotopes of iodine by oxidation, by iodinated reagents that bind to proteins or by binding reagents to the protein that are particularly susceptible to iodination have been described.

Radioisotopes, for example radiometals, can also be attached to proteins through the use of bifunctional coupling agents. These agents bind both the protein and the radioisotope and so join the two. Many examples are known to those skilled in the art. Bifunctional coupling agents which can bind radiometals to a protein and which contain chelators that bind desired radiometals are preferred. It is also preferred that the radiometal remains bound in vivo, and that the loss of the radiometal does not exceed about ten percent/day. Most preferred are bifunctional coupling agents known to bind isotopes of Tc, Re, Cu and Pb to proteins.

Bifunctional coupling agents most preferred in the invention can be described by the formula C-L'-A; wherein C is the chelating portion of the agent, L' is an organic linking radical with at least two sites of attachment for A and C, and A is a reactive site used to attach the agent to the cross-linked target-specific protein composition.

Preferred in the invention are chelating portions, C, containing at least one protected thiol. The thiol-containing chelating portion is suitably protected from reaction with electrophilic sites during attachment of the bifunctional coupling agent to the protein. As used herein, the expression "protected thiol" refers to a thiol containing moiety wherein the thiol group(s) is (are) reversibly derivatized such that the thiol(s) is (are) rendered unreactive. After attachment to the protein, the chelating moiety can be deprotected to unmask the chelating functionality for radiometal binding.

Groups suitable for protecting the thiol from reaction are organic or inorganic groups which can be readily removed under mild conditions to regenerate the free thiol in the presence of the protein without substantially altering the activity of the protein. In a preferred embodiment of the invention, the thiol protecting group is selected from the group consisting of thiol esters, disulfides and Michael-addition products. More preferably the protecting group is a thiol ester.

Most preferably, the chelating moiety, C, is selected from the following formulas:

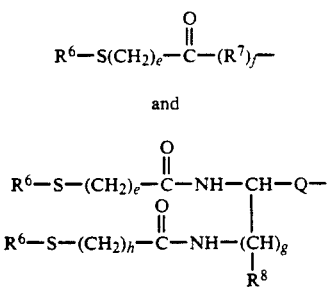

wherein e, g and h are independently selected from integers from 1 to 3 inclusive, and most preferably 1; f is an integer from 3 to 6 inclusive, and most preferably 3; $R^6$ is $R^9CO-$ or $R^9-S-$ wherein $R^9$ is methyl, optionally substituted alkyl, and optionally substituted aryl or heteroaromatic, and most preferably $R^6$ is $R^9CO-$ wherein $R^9$ is phenyl or phenyl substituted with a functional group; each $R^7$ is independently selected from the units:

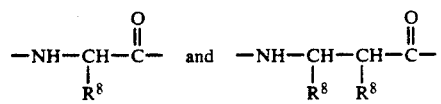

and most preferably $R^7$ is $-NHCH(R^8)CO-$ where each $R^8$ is independently selected from hydrogen, optionally substituted alkyl, optionally substituted aryl or heteroaromatic, and most preferably $R^8$ is hydrogen; and Q is a bond, carbonyl group or $-CHR^8-$.

The organic linking radical L' has at least two valencies for joining C and A. In addition, L' preferably contains one or more cleavable sites. These cleavable sites enhance the clearance of the radiometal from the non-target tissue. As used herein, the expression "cleavable site" refers to a chemical bond in the linking radical, the breaking of which serves to dissociate the radiometal in chelated form from the labeled protein, which bond is known to have an appreciable rate of dissociation in neutral aqueous media or known to have an appreciable rate of dissociation by metabolism in an organ. Such dissociation should preferably occur at a rate of at least about 50% within the half-life of the radiometal.

The cleavable site may be included in the linking radical or may form one of the bonds between L' and either C or A. Preferably the cleavable site is an alkyl ester, an ester of an aryl or heteroaromatic alcohol, or an aryl or heteroaromatic ester of an alkyl alcohol. Preferred linking radicals L' are selected from the group consisting of optionally substituted alkyl, optionally substituted alkyl containing heteroatom substituents for carbon (e.g., in which a carbon in the aliphatic chain is substituted with a heteroatom such as N, O, or S) and optionally substituted aryl groups. Most preferably, the linking radical L' is selected from the following formula:

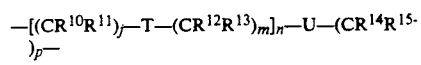

wherein each of $R^{10}$, $R^{11}$, $R^{12}$, $R^{13}$, $R^{14}$ and $R^{15}$ is independently selected from hydrogen, optionally substituted alkyl, optionally substituted aryl or heteroaromatic, and most preferably each of the R groups are hydrogen; m is selected from integers from 0 to 6 inclusive, and preferably m is 2; n is selected from integers from 1 to 6 inclusive, and preferably n is 1; j is independently an integer from 0 to 6 inclusive, and preferably j is 0; p is an integer from 0 to 6 inclusive, with the proviso that when p is 0 and m is 0 then U cannot be $-NH-$, $-O-$, or $-S-$, and preferably p is 2; T is selected from the group consisting of $-NH-$, $-O-$, or $-S-$, and preferably T is $-O-$; and U is selected from the group consisting of a bond, T, $-CH_2CONH-$, $-NHCOCH_2-$, $-OCOCH_2-$ and $-CH_2CO_2-$, and preferably U is $-O-$, provided that when T is $-NH-$, then U is $-CH_2CO_2-$ or $-OCOCH_2-$.

The bifunctional coupling agent is attached to the cross-linked target-specific protein composition through a reactive site A. Suitable reactive sites include groups capable of selective reaction with an amino functionality, sulfhydryls, protein carboxyls or oxidized carbohydrate moieties.

Reactive site A may include, for example, those groups capable of selective reaction with an amino function, such as those selected from the group consisting of an imidate ester, an epoxide and an active ester. As used herein, "active ester" refers to an ester of a carboxylic acid which reacts with amines to form amides at an appreciable rate in aqueous solution at or near neutral pH. Preferred are active esters of N-hydroxysuccinimide or 3-sulfo-N-hydroxysuccinimide.

Reactive site A may also be a group capable of selective reaction with sulfhydryls, including those selected from the group consisting of maleimide, alkyl halide, sulfonate ester and aziridine. Examples include ClCH₂CONH—, BrCH₂COHN—, ICH₂CONH— and most preferably N-substituted maleimides.

Reactive site A may also be a nucleophile capable of reacting with protein carboxyls or oxidized carbohydrate moieties, including those selected from the group consisting of hydroxylamines, hydrazines, hydrazides and amines. Preferred are hydrazides.

The preferred bifunctional coupling agents of the invention are exemplified by the formulae for Compounds III and IV.

position. A protected precursor containing thiol protecting groups is most preferred in the invention.

Bifunctional coupling agents containing protected thiol group(s) and attached to cross-linked target-specific protein compositions is(are) deprotected prior to attachment of the radiometal to form radiotherapeutic and radiodiagnostic agents of the invention. The protecting groups comprised of Michael-addition products can be removed by treatment with mild base. The protecting groups comprised of thiol esters can be removed by treatment with reagents generally known to

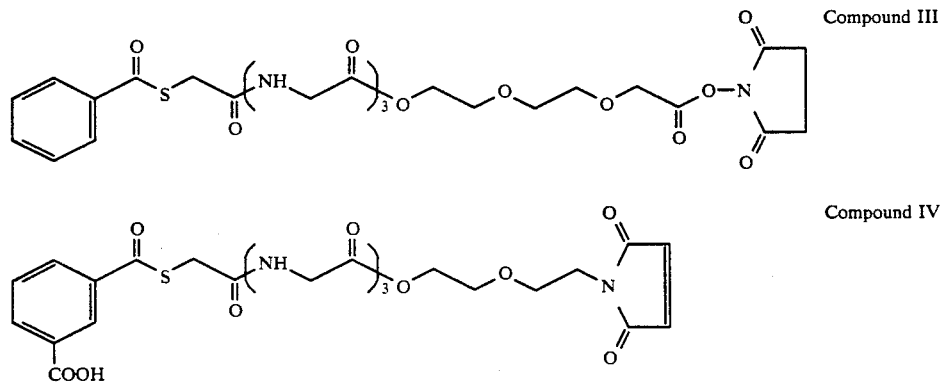

Compound III

Compound IV

The bifunctional coupling agent is joined to the cross-linked target-specific composition through the reactive moiety A. Bifunctional coupling agents containing a nucleophilic moiety A, for example, a substituted hydrazide, are mixed with the cross-linked target-specific protein composition in a suitable buffer and an agent known to form amide bonds in solution, for example 1-3-dimethylaminopropyl-3-ethylcarbodiimide, is added. The compositions containing oxidized carbohydrate need only be mixed with said hydrazide, and optionally stabilized by reduction with sodium cyanoborohydride. Bifunctional coupling agents containing a sulfhydryl-selective moiety A, for example an N-substituted maleimide, are reacted with the cross-linked target-specific protein composition containing one or more sulfhydryls in a suitable buffer, preferably pH 7 to 8. The compositions containing one or more sulfhydryls are prepared by reacting the cross-linked target-specific protein composition with reagents known to introduce sulfhydryls onto proteins, for example 2-iminothiolane. Bifunctional coupling agents containing an amine-selective moiety A, for example an active ester, are reacted with the cross-linked target-specific protein composition in a suitable buffer, preferably between pH 7 and 9.

The most preferred bifunctional coupling agents bind the cross-linked target-specific protein composition and a radiometal or a radionuclide having an affinity for thiols. Useful radiometals include isotopes of Tc, Re, Pb and Cu. The radiometal is generally linked to the chelating moiety C of the bifunctional coupling agent.

As used herein, a "protected precursor" is one or more bifunctional coupling agents containing protected chelating group(s), preferably protected thiol group(s), bound to a cross-linked target-specific protein composition. As used herein, a "precursor" is one or more bifunctional coupling agents without protecting groups, including those prepared from a protected precursor, attached to a cross-linked target-specific protein combe nucleophilic in neutral aqueous solutions, for example, hydroxide, imidazole, hydrazine and substituted hydrazines, hydroxylamine and substituted hydroxylamines, or thiols. A suitable procedure for the removal of a thiol ester would be to treat a volume of the cross-linked target-specific protein composition bound to the bifunctional coupling agent with a volume of 0.5–1.0M hydroxylamine at or near pH 7.5 for a period of five minutes and then purify the composition by gel filtration chromatography, for example. The protecting groups comprised of disulfides can be removed by treatment with thiols, as has been discussed supra.

Precursors of the invention can be used to form new radiotherapeutic or radiodiagnostic agents by addition of a suitable radiometal or radionuclide. The precursors can be used to prepare kits for the preparation of the radiotherapeutic or radiodiagnostic agents by formulation in a suitable matrix. Operation of the kit is comprised of addition of the radiometal and appropriate manipulations to form the radiotherapeutic or radiodiagnostic agent.

Deprotection of the bifunctional coupling agent-cross-linked target specific protein composition provides a thiol-containing chelating functionality for the binding of metals, especially radiometals. The affinity of the deprotected chelating portion for metals is generally high enough that this binding can be accomplished in aqueous solution near neutral pH and at or near ambient temperatures. A pH range of about 5 to 8 and temperatures of about 4° to 37° C. can be used.

Some radiometals require a change in oxidation state prior to complexing with the bifunctional coupling agent. The change in oxidation state can be accomplished either in a separate vessel or in the presence of the bifunctional coupling agent-cross-linked target specific protein composition. Depending on the nature of the radiometal, and the relative speed of complex formation, a transfer-ligand may be required. This transfer-ligand consists of a molecule or mixture capable of weakly complexing the radiometal in a reduced state. This transfer ligand is intended only to transiently stabilize an otherwise relatively unstable intermediate.

The technetium complex of the bifunctional coupling agent can be prepared in this fashion using D-glucaric acid as a transfer ligand. The eluate from a technetium-99m generator is mixed with an equal volume of 2.0 to 30 mg/mL monopotassium D-glucaric acid in 0.2N bicarbonate. A reducing agent is then added, usually a 5 uL/mL addition of 5 mg/mL stannous chloride in 0.2N aqueous acetic acid. After waiting an appropriate length of time for the pertechnetate to reduce and the transfer complex to form, the mixture is mixed with the deprotected bifunctional coupling agent-cross-linked target specific protein composition in a pH of about 7 to 8. The mixture is allowed to sit at or near ambient temperature until more than 90% and usually more than 95%, of the technetium becomes attached to the protein composition. This can be ascertained by a variety of quantitative and qualitative methods, including gel filtration HPLC and thin layer chromatography techniques.

EXAMPLES

Compositions of the invention are illustrated by, but not limited to, the following examples. All temperatures are degrees Celsius. NMR spectra are given for $^1$H at 300 MHz using TMS as an internal standard.

GENERAL METHODS

Compound III

Preparation of succinimidyl 8-carboxy-3,6-dioxaoctyl-2-benzoylthioacetyl)glycyl-glycylglycinate a) Preparation of tert-butyl 8-hydroxy-3,6-dioxaoctanoate.

A solution of 53 g of 2-hydroxyethyl ether (0.5 mol) in 200 mL of tetrahydrofuran was prepared, and the solution cooled in an ice-water bath. The solution was placed under a slow stream of argon. Sodium bis(trimethylsilyl)amide (125 mL, 0.125 mol, 1M in tetrahydrofuran) was added dropwise over a 30 minute period. The mixture was stirred an additional 30 minutes, then 24.4 g of tert-butyl 2-bromoacetate (0.125 mol) was added. The mixture was then stirred for 1 hour. The ice-water bath was removed, and the mixture transferred to a separatory funnel using 250 mL of 1M NaH$_2$PO$_4$. The mixture was extracted with ethyl acetate (3×150 mL). The combined extracts were dried over sodium sulfate, filtered, and the solvent removed by rotary evaporator to give a clear yellow liquid. The liquid was purified by chromatography using 500 mL of silica gel and eluting with ethyl acetate/hexanes 1:1. The product was isolated as a clear, gold liquid. Obtained 5.49 g TLC R$_f$ 0.50 (EtOAc). NMR (DMSO-d$_6$) δ 1.42 (s, 9H), 3.42 and 3.54 (m, 8H), 3.98 (s, 2H).

b) Preparation of 8-tert-butyloxy-8-oxo-3,6-dioxaoctyl (2-benzoylthioacetyl)glycylglycylglycinate.

To a solution of 3.69 g of (2-benzolylthioacetyl)-glyclyglycylglycine (10 mmol, prepared as above) in 50 mL of dimethylformamide was added 0.12 g of 4-dimethylaminopyridine (1 mmol), 2.05 g of tert-butyl 8-hydroxy-3,6-dioxaoctanoate (10 mmol, prepared as above) and 2.07 g of dicyclohexylcarbodiimide (10 mmol). The initially clear solution developed a precipitate with time. The mixture was stirred at room temperature for 60 hours. The solids were removed by filtration. The solvent was removed from the filtrate by rotary evaporator (vacuum pump, bath temperature 40°) to give the product as a yellow wax. This wax was taken up in 175 mL of boiling 2-propanol, filtered hot, and the solution let cool to room temperature. The product precipitated out as a beige solid. This solid was filtered off and dried under vacuum over P$_2$O$_5$ to give 2.97 g (52%) TLC R$_f$ 0.31 (chloroform/2-propanol 9:1). NMR (DMSO-d$_6$) δ 1.42 (s, 9H), 3.58 (m, integral obscured by water peak), 3.78 (m, 4H), 3.89 (s, m, 4H), 3.99 (s, 2H), 4.15 (m, 2H) 7.58 (m, 2h), 7.71 (t, 1H), 7.95 (m, 2H), 8.25 (m, 2H), 8.48 (m, 1H).

c) Preparation of 8-succinimidyloxy-3,6-dioxa-8-oxo-octyl (2-benzoylthioacetyl)glycylglycylglycinate (Compound III).

A solution of 8-tert-butyloxy-3,6-dioxa-8-oxooctyl (2-benzoylthioacetyl)glycylglycylglycinate (2.71 g, 5.89 mmol, prepared as above) was prepared in 7 mL of trifluoroacetic acid. The clear solution was stirred for 1 hour at room temperature. The trifluoraoacetic acid was removed by rotary evaporator (water aspirator, bath temperature 25°). The residual oil was taken up several times in chloroform and the solvent removed by rotary evaporator. The residue was dried under vacuum overnight to give a yellow solid. NMR spectroscopy confirmed the loss of the tert-butyl ester. The solid was dissolved in 50 mL of dimethylformamide/tetrahydrofuran 1:1. To the solution was added 0.06 g of 4-dimethylaminopyridine (0.49 mmol), 0.56 g of N-hydroxysuccinimide (4.9 mmol) and 2.02 g of dicyclohexylcarbodiimide (9.8 mmol). The solution was stirred for 48 hours at room temperature. An additional 0.5 g of dicyclohexylcarbodiimide was then added, and the mixture stirred an additional 5 hours at room temperature. The resultant solids were filtered off, and the solvents removed from the filtrate by rotary evaporator (water aspirator followed by vacuum pump, bath temperature ≦40°) to give the product as an oil. The oil was dried under vacuum overnight to give a brown colored wax. The wax was taken up in 85 mL of hot 2-propanol, filtered while hot and allowed to cool to room temperature. The product precipitated out and was collected by filtration. Drying under vacuum gave 1.0 g of a beige powder (34%). R$_f$ 0.77 (butanol/acetic acid/water 5:2:3). NMR (DMSO d$_6$) δ 2.83 (s, 4H), 3.61 (m, 6H), 3.77 (m, 4H), 3.89 (s+m, 4H) r.16 (m, 2H), 4.62 (s, 2H), 7.58 (m, 2H), 7.71 (t, 1H), 7.93 (m, 2H), 8.26 (m, 2H), 8.49 (m, 1H).

Compound IV

Preparation of 2-(2-maleimidoethoxy)ethyl (2-(3-carboxybenzoylthio)acetyl)glycylglycylglycinate a) Preparation of 2-(3-tert-butyloxycarbonyl-benzoylthio)acetyl)glycylglycylglycine.

A solution of triglycine (0.53 g, 2.8 mmoles) and NaHCO$_3$ (0.26 g, 3.0 mmoles) in water (10 mL) was cooled in an ice bath and treated with a solution of succinimidyl 3-tert-butyloxycarbonylbenzoate (1.1 g, 2.8 mmoles) Fritzberg, A. R. Eur. Pat. Appl. 86100360.6) in THF (10 mL). After stirring at 0° C. for 30 minutes, the mixture was stirred at room temperature for 1 hour. THF was removed under reduced pressure, and the aqueous mixture was acidified to pH 3 with 1N HCl. The resulting precipitate was collected and recrystallized from aqueous acetone (0.55 g, 42%). NMR (DMSO-d$_6$) δ 1.57 (s, 9H), 3.75 (m, 6H), 3.94 (s, 2H), 7.73 (t, 1H), 8.20 (m, 4H), 8.38 (s, 1H), 8.55 (t, 1H).

b) Preparation of 2-(2-maleimidoethoxy) ethanol.

A solution of 2-(2-aminoethoxy)ethanol (1.35 g, 12 mmoles) in saturated NaHCO$_3$(65 mL) was cooled in an ice bath and treated with N-methoxycarbonyl maleimide (2.00 g, 12 mmoles). After 20 minutes, the ice bath was removed and the solution was stirred at room temperature for 30 minutes. The solution was extracted with CHCl$_3$ (3×50 ml) and the combined extracts were dried (Na$_2$SO$_4$). Removal of the solvent under reduced pressure gave the maleimido alcohol as an oil (1.70 g, 71%). NMR (CDCl$_3$) δ 2.32 (t, 1H, -OH), 3.54 (m, 2H), 2.64 (m, 6H), 6.72 (s, 2H).

c) Preparation of 2-(2-maleimidoethoxy)ethyl (2-(3-tertbutyloxycarbonylbenzoylthio)acetyl)glycylglycinate.

The above maleimido alcohol (80 mg, 0.43 mmoles) in CH$_2$Cl$_2$ (2 mL), cooled by an ice bath, was treated with 2, 6 di-t-butyl-4-methylpyridine (90 mg, 0.43 mmoles) followed by trifluoromethanesulfonic anhydride (120 mg, 0.43 mmoles) in CH$_2$Cl$_2$ (1 mL). After stirring 1 hour the precipitate was removed by filtration, and the filtrate was added to a solution of (2-(3-tert-butyloxycarbonylbenzoylthio)acetyl)glycyl-glycylglycine (200 mg, 0.43 mmoles) and diisopropylethylamine (75 μL, 0.43 mmoles) in CH$_2$Cl$_2$ (2 mL). After stirring for 2 hours the mixture was concentrated and chromatographed (SiO$_2$, CHCl$_3$-CH$_3$OH gradient) to give the ester (70 mg, 26%). NMR (CDCl3) δ 1.61 (s, 9H), 3.63 (m, 6H) 3.85 (s, 2H), 4.02 (m, 6H), 4.22 (t, 2H), 6.72 (s, 2H), 7.21 (t, 1H), 7.40 (t, 1H), 7.44 (t, 1H), 7.52 (t, 1H), 8.09 (d, 1H), 8.20 (d, 1H) 8.54 (s, 1H).

d) Preparation of 2-(2-maleimidoethoxy)ethyl (2-(3-carboxybenzoylthio)acetyl)glyclyglycylglycinate.

The tripeptide ester prepared above (60 mg, 0.09 mmoles) was stirred with triflouroacetic acid (2 mL) for 2 hours. TFA was removed at the vacuum pump to yield an oil which precipitated from CH$_3$OH to give the produce (50 mg, 91%). NMR (DMSO-d$_6$) δ 3.58 (m, 6H), 3.79 (m, 6H), 3.92 (s, 2H), 4.08 (m, 2HO, 7.03 (s, 2H), 7.72 (t, 1H), 8.21 (m, 3H), 8.43 (s, 1H), 8.52 (m, 1H).

Antimyosin Preparation

Antimyosin F(ab')$_2$ was prepared from the IgG by lysl endopeptidase digestion, and purified by chromatography on Protein A-Sepharose ™ and S-Sepharose Fast Flow ™. Antiovarian cancer OC125 F(ab')$_2$ was prepared by pepsin digestion of the IgG, followed by purification on Protein A-Sepharose ™ and S-Sepharose Fast Flow ™.

Antimyosin and OC125 Fab' were prepared by reduction of the respective F(ab')$_2$ with 10 mM dithiothreitol. The reduced Fab' was purified by chromatography on Sephadex G-25M (PD-10 column), eluting with 0.10M phosphate buffer pH 7.00 containing 1 mM EDTA. Aliquots (50 μL) of fractions were diluted to 1.0 mL with 0.10M phosphate buffer pH 8.10 containing 1 mM EDTA. The diluted fractions were used to monitor protein concentration (OD280) and for sulfhydryl analysis. Sulfhydryl analyses were performed using 5,5'-dithiobis (2-nitrobenzoic acid)(Ellman's reagent). For the Fab': E280 (1%)=14.0 and MW=50,000; for the F(ab')$_2$: E280 (1%)=14.0 and MW=100,000.

Compound III/IV-Protein Conjugate Labeling Procedure

The deprotected Compound III-protein conjugate and the deprotected compound IV-protein conjugate were labeled with Tc-99 m by the following procedure.

To a Sn-glucarate vial (containing lyophilized 150 μg SnC12.2H$_2$O and 6 mg monopotassium glucarate) was added 2.0 mL of [Tc-99 m]TcO$_4$(Mo-99/Tc-99 m generator eluate, diluted to the appropriate specific activity with 0.9% saline, 40–100 mCi), and mixed. After 5 minutes at room temperature, 0.5–1.0 mL of the [Tc-99m]Tc-glucarate was withdrawn and added to 1.0 mL of the protein conjugate (0.3–1.0 mg) in 0.10M phosphate buffer pH 7.00 containing 1 mM EDTA. Aliquots (10 μL) were removed at 15 and 30 minutes and tested for extent of labeling by ITLC. The aliquots were spotted onto 1×10 cm silica gel ITLC plates and developed with 0.10M citrate pH 5.0. The plates were then cut in half and activity measured in a dose calibrator. The % protein bound was determined by:

$$\frac{\text{activity top half}}{\text{activity top half + activity bottom half}} \times 100 = \%$$

Extent of labeling was also checked by gel filtration HPLC on a Zorbax ™ GF-250 column after reacting a 200 μL sample of the labeled protein with 5 μL of 0.05M N-ethyl maleimide in 5% DMF/0.15% saline.

EXAMPLE 1:

Preparation of Cross-Linked OC125 F(ab')$_2$—Compound III Conjugate a. Preparation of 2,2'-N,N'-bis-maleimidoethyl ether (Compound II)

To a solution of 1.0 g of 2,2'-oxybis(ethylamine) dihydrochloride in 50 mL of saturated NaHCO$_3$ at 0° were added 1.93 g of N-methoxycarbonylmaleimide. The heterogenous mixture was stirred at 0° for 15 minutes, then stirred at room temperature for 1 hour. Water (100 mL) was added and stirring continued for an additional 40 minutes. The pH was adjusted to ca. 4 with 12N HCl. The solution was concentrated to 40 mL, and re-acidified to a pH of about 3. The solution was extracted with 20% 2-propanol in chloroform (3×50 mL). The combined extracts were dried over Na$_2$SO$_4$, filtered, and the solvent removed to give 0.72 g of a white solid. This solid was purified on 120 mL of silica gel, eluting with chloroform. Fractions containing the pure product were combined and solvent removed to give 0.20 g of a white solid. TLC R$_f$0.18(CHCl$_3$). NMR (300 MHz, DMSO-d$_6$) δ (m, 8.8 H), 6.99(s, 3.6 H).

b. Preparation of Cross-Linked OC125 F(ab')$_2$

To 11.2 mg of OC125 Fab' in 2.85 mL of 0.10M phosphate buffer pH 7.00 containing 1 mM EDTA (3.75 mole SH/mole) were added 2.2 mg of Compound II in 0.14 mL of DMF. The solution was mixed, and stood for 1 hour at room temperature. The alkylated Fab' was purified on a 1×17 cm Sephadex G-25 M column, eluting with 0.10M phosphate buffer pH 7.00 containing 1 mM EDTA. Fractions containing protein were identified by OD280 as described above and pooled to give 10 mg of alkylated Fab' in 7.6 mL. To the alkylated Fab' was added 10.6 mg of freshly prepared OC125 Fab' in 2.85 mL of 0.10M phosphate buffer pH 7.00 containing 1 mM EDTA (3.71 mole SH/mole), and mixed. The solution stood for 64 hours at 4°. The solution was concentrated to 2.75 mL. To the solution was added 0.28 mL of 100 mM DTT in 0.10M phosphate buffer pH 7.00 containing 1 mM EDTA. The solution was mixed then stood for 1.5 hours at room temperature. Iodoacetamide (10.4 mg) in 0.28 mL of DMF was then added, and the solution mixed, then stood for 1.5 hours at room temperature. The mixture was purified on a 2.6×61 cm column of Sephacryl S-200, injecting 0.5 mL aliquots of the cross-linked protein solution and eluting at 1.0 mL/minute with 0.10M phosphate buffer pH 7.00 containing 1 mM EDTA. Fractions containing the cross-linked OC125 F(ab')$_2$ were combined and concentrated to give 2.8 mg in 0.5 mL. Gel filtration HPLC on a Zorbax GF-250 column eluted at 1.0 mL/minute gave the following retention times, area percent given in parenthesis; OC125 F(ab')$_2$ standard, 9.09 min (100%); OC125 Fab' standard, 9.99 min (100%); cross-linked OC125 F(ab')$_2$, 9.10 min (92%) 9.98 min (8%).

c. Conjugation of Cross-Linked OC125 F(ab')$_2$ with Compound III. Deprotection and Tc-99 m Labelling To 2.3 mg of the cross-linked OC125 F(ab')$_2$ in 0.41 mL of 0.10M phosphate buffer pH 7.00 containing 1 mM EDTA were added 0.243 mg of Compound III in 20 μL of DMF. The solution was mixed, then stood for 1 hour at room temperature. The mixture was purified on a 1×17 cm Sephadex G-25 M column, eluting with 0.10M phosphate buffer pH 7.00 containing 1 mM EDTA. Fractions containing the protein were determined by OD280 as described above. A fraction (0.95 mL) containing 2.21 mg of the cross-linked F(ab')$_2$-Compound III conjugate was obtained. Gel filtration HPLC gave a single broad peak running from 9.0 min. The conjugate (1.77 mg in 0.80 mL) was deprotected by the addition of 0.08 mL of 100 mM DTT in 0.10M phosphate buffer pH 7.00 containing 1 mM EDTA, mixing, and standing for 1 hour at room temperature. The deprotected material was purified on a 1×17 cm Sephadex G-25 M column, eluting with 0.10M phosphate buffer pH 7.00 containing 1 mM EDTA. Fractions containing the deprotected conjugate were detected as described above. A fraction (0.95 mL) containing 1.1 mg of protein having 2.88 mole SH/mole was obtained. To a Sn-glucarate vial was added 1.0 mL of [Tc-99 m]TcO$_4$. The contents were mixed, and after 10 minutes 0.5 mL of the [Tc-99 m]Tc-glucarate was added to 0.50 mL of the deprotected cross-linked F(ab')$_2$-Compund III conjugate. The solution was mixed, then stood for 30 min at room temperature. Labeling by ITLC was 99.9%. Gel filtration HPLC gave three protein peaks by UV detection; 8.254 min (23.9%), 9.03 min (66.9%) and 9.93 min (9.1%), and two protein peaks by radiometric detection; 8.33 min (33.7%) and 9.22 min (66.3%).

EXAMPLE 2

Preparation of Cross-Linked antimyosin F(ab')$_2$-Compound IV Conjugate a. Preparation of Cross-Linked Antimyosin F(ab')$_2$ To a solution of antimyosin Fab' (2.85 mL, 9.62 mg/mL, 3.31 mol SH/mol) was added 143 μL of a solution containing 30.3 mg/mL of N,N'-bis-maleimidomethyl ether (Compound II) in dimethylformamide. The Fab'-bismaleimidomethyl ether solution was mixed gently, and let stand for 2 h at room temperature. The Fab'-bismaleimidomethyl ether conjugate was purified in two 1.5 mL aliquots on a 1×16 cm Sephadex G 25 M column. Fractions containing the conjugate were combined to give a total of 27.2 mg of protein in 7.60 mL. To the conjugate was added a solution of freshly prepared antimyosin Fab' (6.96 mg/mL, 3.80 mL, 3.34 mol SH/mol), and the combined solutions mixed, then stored at 2°-8° C. for 65 h. The cross-linked antimyosin F(ab')$_2$ solution was concentrated to a volume of 3.0 mL. To the solution was added 0.30 mL of 0.10M dithiothreitol in 0.10M phosphate pH 7.00 containing 1 mM EDTA. The solution was mixed, then stood for 2.5 h at room temperature. To the solution was then added 0.30 mL of 37.0 mg/mL iodoacetamide in dimethylformamide. The solution was mixed, then stood for 2.5 h at room temperature followed by 16 h at 2°-8° C. The cross-lined antimyosin F(ab')$_2$ was purified on a 2.6×61 cm Sephacryl S-200 column, eluting with 0.02M phosphate pH 7.0 containing 0.9% sodium chloride. A fraction (6 mL) containing 7.2 mg of pure cross-linked antimyosin F(ab')$_2$ was obtained. Gel filtration HPLC (Zorbax GF-250): retention time, min (area percent): 8.77 (100). F(ab')$_2$ standard: 8.78 min. Fab': 9.82 min.

b. Cross-Linked Antimyosin F(ab')$_2$ Linked to Compound IV using 2-iminothiolane To a 0.5 mL aliquot of the cross-linked antimyosin solution (0.6 mg) was added 50 μL of a solution of 3.0 mg/mL 2-iminothiolane hydrochloride in 0.10M phosphate pH 7.0 containing 1 mM EDTA. The cross-linked F(ab')$_2$ solution was mixed, then stood at room temperature for 1.75 h. The 2-iminothiolane modified protein was then purified on Sephadex G 25 M eluting with 0.10M phosphate pH 7.0 containing 1 mM EDTA, giving a fraction containing 0.3 mg of protein in 0.95 mL and having 6.75 mol SH/mol by Ellman's assay. To this fraction was added 0.19 mL of a 0.68 mg/mL solution of Compound IV in 40% ethanol. The solution was mixed, then stood for 1 h. The cross-linked antimyosin F(ab')$_2$-2-iminothiolane-Compound IV conjugate was then purified on a Sephadex G 25 M column, giving a fraction containing 0.17 mg of the modified protein. This material gave a single peak on gel filtration HPLC (8.73 min). F(ab')$_2$ standard; 8.78 min. Binding of the cross-linked antimyosin F(ab')$_2$ and the cross-linked antimyosin F(ab')$_2$-2-iminothiolane-Compound IV conjugate to canine cardiac myosin was determined by a enzyme linked immunoassay together with the antimyosin Fab as a standard. Results are expressed as -log of the concentration (mg/mL) required to achieve 50% inhibition. It was found that the Fab standard was 3.6±0.2; cross-linked antimyosin F(ab')$_2$ 3.84±0.2; and cross-linked antimyosin F(ab')$_2$-2-iminothiolane-Compound IV conjugate 4.03±0.2.

What is claimed is:

1. A cross-linked protein composition comprising at least two proteins specific to a target joined by at least one sulfhydryl-selective cross-linking agent, said sulfhydryl-selective cross-linking agent being bound to sulfhydryl groups on the target specific proteins, wherein said sulfhydryl-selective cross-linking agent is represented by Compound I or Compound II as follows:

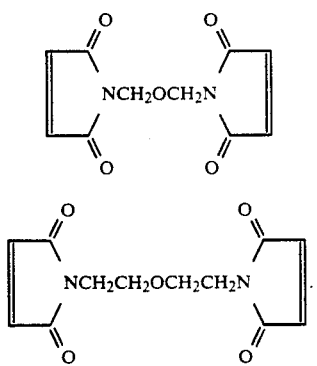

Compound I

Compound II

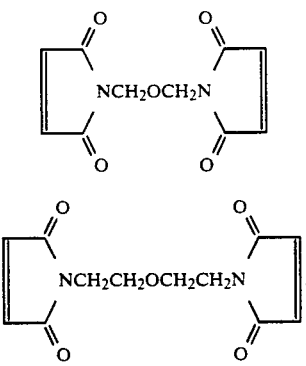

Compound I

Compound II

2. The cross-linked protein composition of claim 1 wherein said target-specific proteins are antibody fragments.

3. The cross-linked protein composition of claim 2 wherein said antibody fragments are Fab' antibody fragments.

4. A method of making a cross-linked protein composition having at least two identical binding sites comprising:
(a) providing a target-specific protein;
(b) contacting said target specific protein with an excess of cross-linking agent to produce target specific protein bound to said cross-linking agent;
(c) removing excess, unbound cross-linking agent; and
(d) adding fresh target protein to the target specific protein bound to said cross-linking agent; wherein said cross-linking agent is represented by Compound I or Compound II as follows:

5. The method of claim 4 including providing antibody fragments as said target-specific protein.

6. The method of claim 5 including providing Fab' antibody fragments as said antibody fragments.

7. The method of claim 4 wherein a thiol-containing agent is added to the product of step (d) in an amount sufficient to reduce remaining disulfides in the cross-linked protein composition.

8. The method of claim 4 wherein a sulfhydryl reactive agent is added to the product of step (d) in an amount sufficient to bond to any unreacted sulfhydryl reactive sites in the cross-linked protein composition.

9. The method of claim 7 where said thiol-containing agent is selected from the group consisting of cysteine and dithiothreitol.

10. The method of claim 8 where said sulfhydryl reactive agent is selected from the group consisting of iodoacetamide and N-ethylmaleimide.

* * * * *

UNITED STATES PATENT AND TRADEMARK OFFICE
CERTIFICATE OF CORRECTION

PATENT NO.  : 5,185,433
DATED       : February 9, 1993
INVENTOR(S) : DEAN ET AL.

It is certified that error appears in the above-identified patent and that said Letters Patent is hereby corrected as shown below:

Title page, Column 1, Line 3 delete "CROSS-LINKING" and insert therefor --CROSS-LINKED--.

Title page, Column 2, Lines 20 and 21, delete "*Attorney, Agent or Firm*-Woodcock Washburn Kurtz Mackiewicz & Morris" and insert therefor --*Attorney, Agent or Firm*-Woodcock Washburn Kurtz Mackiewicz & Norris--.

Column 6, Line 43 delete "knwon" and insert therefor --known--.

Column 9, Line 2 delete "$BrCH_2COHN-$," and insert therefor --$BrCH_2CONH-$---.

Column 13, Line 32 delete "glyclyglycylglycinate." and insert therefor --glycylglycylglycinate.--.

Column 13, Line 34 delete "triflouroacetic" and insert therefor --trifluoroacetic--.

Column 13, Line 37 delete "produce" and insert therefor --product--.

Signed and Sealed this

Twenty-first Day of December, 1993

*Attest:*

BRUCE LEHMAN

*Attesting Officer*     Commissioner of Patents and Trademarks